United States Patent [19]

Orban

[11] Patent Number: 5,688,969
[45] Date of Patent: Nov. 18, 1997

[54] PROCESS FOR THE PREPARATION OF THIOPHENE-2-5-DICARBOXYLIC ACID AND THE DICHLORIDE THEREOF

[75] Inventor: Ivan Orban, Basel, Switzerland

[73] Assignee: Ciba Specialty Chemicals Corporation, Tarrytown, N.Y.

[21] Appl. No.: 751,566

[22] Filed: Nov. 18, 1996

Related U.S. Application Data

[63] Continuation of Ser. No. 517,889, Aug. 21, 1995, abandoned.

[30] Foreign Application Priority Data

Aug. 25, 1994 [CH] Switzerland ............... 2607/94

[51] Int. Cl.$^6$ .................................. C07D 333/40
[52] U.S. Cl. ........................................ 549/71
[58] Field of Search ................................ 549/71

[56] References Cited

U.S. PATENT DOCUMENTS

| | | | |
|---|---|---|---|
| 2,744,917 | 5/1956 | Jones et al. | 549/71 |
| 3,062,834 | 11/1962 | Fiesselmann | 549/71 |
| 3,127,416 | 3/1964 | Liechti et al. | 549/71 |
| 5,093,504 | 3/1992 | Goda et al. | 549/71 |
| 5,310,940 | 5/1994 | Goda et al. | 549/71 |

FOREIGN PATENT DOCUMENTS

| | | |
|---|---|---|
| 1210888 | 2/1966 | Germany. |
| 129448 | 1/1978 | Germany. |
| 426870 | 6/1967 | Switzerland. |

OTHER PUBLICATIONS

Derwent Abs. No. 78–25397A/14 of DD–12944–A, Raunen et al, "Pure thiophene-2–5–dicarboxylic and . . . ", (1978).
Chem. Abst. 57:15075 of DE 1,210,888, (1962).
Chem. Abst. 89:753479 of DD 129,448, (1978).
Chem. Abst. 68:871432 of CH 426,870, (1968).

Primary Examiner—José G. Dees
Assistant Examiner—Deborah Lambkin
Attorney, Agent, or Firm—Michele A. Kovaleski; Victoria M. Malia; Luther A. R. Hall

[57] ABSTRACT

The invention relates to a process for the preparation of thiophene-2,5-dicarboxylic acid by reacting thionyl chloride and adipic acid, with pyridine as catalyst, which process comprises A) adding 1 part of adipic acid to 3 to 6 parts of thionyl chloride, mixed with a catalytic amount of pyridine,
B) adding a further 4 to 7 parts of thionyl chloride in the temperature range from 85° to 95° C.,
C) removing excess thionyl chloride and volatile by-products under reduced pressure, and
D) bringing the reaction to completion in the temperature range from 140° to 160° C., and
E) preparing a salt of thiophene-2,5-dicarboxylic acid by hydrolysing the chloride obtained with an aqueous solution of an alkaline earth metal hydroxide or an alkali metal hydroxide, and
F) obtaining the free acid from this salt with a mineral acid.

7 Claims, No Drawings

PROCESS FOR THE PREPARATION OF THIOPHENE-2-5-DICARBOXYLIC ACID AND THE DICHLORIDE THEREOF

This application is a continuation of application Ser. No. 08/517,889, filed Aug. 21, 1995, abandoned.

The invention relates to a process for the preparation of thiophene-2,5-dicarboxylic acid and the dichloride thereof.

Thiophene-2,5-dicarboxylic acid is typically used as intermediate in the preparation of fluorescent whitening agents. For this purpose it must be obtained in a specific purity. A number of processes are known for its preparation which proceed via the dichloride of this acid as intermediate.

An illustrative example of such a process is disclosed in patent specification DD-B-129 448: Thionyl chloride and adipic acid, with pyridine as catalyst, are heated together, to give the acid chloride, which is hydrolysed with sodium hydroxide solution, and the acid is then precipitated with a mineral acid.

It has now been found that this process can be materially improved.

Accordingly, the invention relates to a process for the preparation of the dichloride of thiophene-2,5-dicarboxylic acid by reacting thionyl chloride and adipic acid with pyridine as catalyst, which process comprises
A) adding 1 part of adipic acid to 3 to 6 parts of thionyl chloride, mixed with a catalytic amount of pyridine,
B) adding a further 4 to 7 parts of thionyl chloride in the temperature range from 85° to 95° C.,
C) removing excess thionyl chloride and volatile by-products under reduced pressure, and
D) bringing the reaction to completion in the temperature range from 140° to 160° C.
E) By hydrolysing the resultant chloride, it is possible to prepare a salt of thiophene-2,5-dicarboxylic acid with an aqueous solution of alkaline earth metal hydroxide or alkali metal hydroxide and
F) to obtain the free acid from this salt by adding a mineral acid. Accordingly, the invention also relates to a process for the preparation of thiophene-2,5-dicarboxylic acid and salts thereof.

In step A it is convenient to add 1 part of adipic acid to the 4- to 5-fold amount of thionyl chloride, and, in step B, a further 5 to 6 parts of thionyl chloride, based on adipic acid, are added.

In step A pyridine is used in catalytic amounts. It is preferred to use 0.05 to 0.2 mol and, more preferably, 0.08 to 0.12 mol, of pyridine per mol of adipic acid.

In step A the temperature is conveniently in the range from 20° to 90° C., preferably from 30° to 60° C.; and in step B it is preferably in the range from 87° to 93° C.

In the distillation step C it is expedient to first distill off excess thionyl chloride under a pressure of up to c.200 mbar and then to reduce the pressure further to 50 to 10 mbar, preferably to 40 to 20 mbar, the temperature being in each case in the range from e.g. 80° to 110° C., preferably from 90° to 105° C. and, most preferably, from 90° to 100° C.

After distillation, the underpressure is conveniently released and processing is preferably continued at normal pressure. Step D is usefully carried out at 140° to 160° C., preferably at c. 150° C. The acid chloride so obtained can be isolated in conventional manner, typically by physical methods such as chromatography or distillation. The acid chloride is preferably distilled off under reduced pressure.

In the saponification step E the acid chloride is conveniently stirred into aqueous alkali (a solution of an alkali metal hydroxide or an alkaline earth metal hydroxide). Suitable alkalies are typically sodium hydroxide solution or potassium hydroxide solution and, preferably, a c. 8 to 15% solution of sodium hydroxide.

The free acid is obtained from the resultant salt by acidification with a mineral acid (step F), suitably a strong mineral acid such as hydrochloric, sulfuric or phosphoric acid, preferably sulfuric acid. In a preferred embodiment of the invention, the solution is first weakly acidified to pH 2 to 5,5, preferably to pH 4 to 5,2, and turbid matter is removed by filtration before further acid is added, whereupon the salt precipitates from the solution.

The novel process described in this application is essentially more suitable for industrial use than the process disclosed in DD-B-129 448 for the following reasons:

The reaction times are substantially shorter in the process of this invention. If, for example, the adipic acid is treated, as described above, with the thionyl chloride for about 20 hours (steps A, B), yields are obtained that are already excellent, whereas the corresponding time in the Working Example of DD-B-129 448 is 67 hours. The difference is even more marked in distillation step C: The slow distillation of c. 25 hours is an essential part of the process of DD-B-129 448, while in the process of this invention a distillation time of typically only 1 to 2 hours suffices.

The volume yield in steps A to D has been doubled compared with that of the process of DD-B-129 448: The initial maximum volume when using 1 mol of adipic acid is 400 ml (owing to the decomposition of the thionyl chloride the volume does not increase during further processing), whereas it is 880 ml the Working Example of DD-B-129 448.

Despite shorter reaction times and, viewed over the whole period of time, temperatures which are on average lower, the obtainable yield of 55% of theory is, surprisingly, higher than in the process of DD-B-129 448 (49%).

For the reasons stated above, the process of this invention affords materially enhanced possibilities for carrying out the synthesis of thiophene-2,5-dicarboxylic acid industrially on a large scale.

The compounds prepared according to the novel process are used, for example, as intermediates in the preparation of fluorescent whitening agents. By reacting the dicarboxylic acid with ortho-aminophenols it is possible to prepare e.g. fluorescent whitening agents and fluorescent dyes of the series of the bis(benzoxazoles) (q.v. for example U.S. Pat. No. 3,127,416).

It is also possible to obtain thiophene-2,5-dicarboxylic acid direct from the acid chloride obtained after step D by splitting off two molecules of HCl. This can be effected by heating to 90°–100° C., as disclosed in CH-B-426 870. If this is done in the presence of suitable reactants such as the above-mentioned ortho-aminophenols, then fluorescent whitening agents may be prepared direct from the dicarboxylic acid chloride.

Accordingly, the advantages of the novel process also promote the direct preparation of the dicarboxylic acid from the dichloride of the dicarboxylic acid. The preferred embodiment here is that wherein the salts of the dicarboxylic acid are. formed as intermediates (step E).

The following Examples illustrate the invention in more detail, but imply no restriction to what is described therein. In these Examples as well as throughout the remainder of the description, parts and percentages are by weight, unless otherwise stated.

EXAMPLE 1

Into a reaction vessel, equipped with stirrer, thermometer, condenser, dropping funnel and inert gas inlet, are put 655 g of thionyl chloride (5.5 mol) and 11 g of pyridine (0.14 mol) and the mixture is heated to 30°–35° C. 204.4 g of adipic acid (1.4 mol) are added at this temperature over 1 hour with a feeder for solids. The escaping hydrochloric acid/sulfur dioxide gas mixture is led off through a small packed column and a reflux condenser mounted thereon and absorbed.

The reaction mixture is heated to a reflux temperature of 90° C., and then a total of 907 g of thionyl chloride (7.6 mol) are added over 20 h such that good reflux is maintained in the flask, the temperature in the flask being a constant 90° C. Excess thionyl chloride is then distilled off at 90°–100° C./1000–200 mbar and the sulfur monochloride so obtained is distilled off at 100° C./200-20. The pressure is released with nitrogen and the distillation residue is heated over 45 minutes to 150° and kept at this temperature for 3 hours.

190 g of the acid chloride of thiophene-2,5-dicarboxylic are distilled off as a yellowish oil at 132°–142° C./7–8 mbar. The hot melt (c. 100° C.) of the acid chloride (m.p. 45°–47° C.) is added incrementally, with stirring, in the temperature range from 40°–50° C. to a mixture of 1600 g of water and 490 g of a 30% solution of sodium hydroxide. The solution so obtained is adjusted with c. 47 g of sulfuric acid to pH 4.8–5.0 and then clarified with 13 g of activated carbon and 30 g of a filtration aid (Kieselgur Clarcel Dif B). To the clarified filtrate are then added dropwise 89 g of sulfuric acid (93%) in the temperature range from 20° to 25° C. The fine beige crystals so obtained are isolated by filtration, washed with water and dried, giveing 133 g of thiophene-2,5-dicarboxylic acid (55% of theory). Purities of 96–99% are obtained by titration and GC analysis. M.p.: 324°–330° C.

What is claimed is:

1. An improved process for the preparation of the dichloride of thiophene-2,5-dicarboxylic acid by reacting thionyl chloride and adipic acid with pyridine as catalyst, wherein the improvement comprises
   A) adding 1 part of adipic acid to 3 to 6 parts of thionyl chloride, mixed with a catalytic amount of pyridine,
   B) adding a further 4 to 7 parts of thionyl chloride in the temperature range from 85° to 95° C.,
   C) removing excess thionyl chloride and volatile by-products under reduced pressure, and
   D) bringing the reaction to completion in the temperature range from 140° to 160° C.
wherein the reaction time in steps A up to and including D is below 30 hours in a 1–2 molar batch.

2. An improved process according to claim 1, wherein the improvement further comprises preparing after steps A to D
   E) a salt of thiophene-2,5-dicarboxylic acid by hydrolysing the chloride obtained with an aqueous solution of an alkaline earth metal hydroxide or an alkali metal hydroxide.

3. An improved process according to claim 2, wherein the improvement further comprises obtaining after steps A to E
   F) the free acid from the salt of thiophene-2,5-dicarboxylic acid by reaction with a mineral acid.

4. An improved process according to claim 1, which comprises using in step A 0.05 to 0.2 mol of pyridine per mol of adipic acid.

5. An improved process according to claim 1, wherein the temperature in step A is in the range from 20° to 90° C.

6. An improved process according to claim 1, wherein the temperature in step B is in the range from 87° to 93° C.

7. An improved process according to claim 1, wherein distillation step C is carried out under a pressure of 10-50 mbar and in the temperature range from 80° to 110° C.

* * * * *